United States Patent [19]
Cook et al.

[11] Patent Number: 5,919,451
[45] Date of Patent: Jul. 6, 1999

[54] METHOD OF IMPROVING THE GROWTH OR THE EFFICIENCY OF FEED CONVERSION OF AN ANIMAL AND COMPOSITIONS FOR USE THEREIN

[75] Inventors: Mark E. Cook, Madison, Wis.; Daria L. Jerome, Frazee, Minn.

[73] Assignee: Wisconsin Alumni Research Foundation, Madison, Wis.

[21] Appl. No.: 09/037,690

[22] Filed: Mar. 10, 1998

Related U.S. Application Data

[63] Continuation-in-part of application No. 08/684,785, Jul. 22, 1996, Pat. No. 5,725,873.

[51] Int. Cl.⁶ .......................... A61K 39/395; A23J 3/12; A23J 1/06; A23K 1/16
[52] U.S. Cl. .................... 424/130.1; 424/157.1; 424/158.1; 424/442; 106/124.1; 426/89; 426/140; 426/657; 530/388.2
[58] Field of Search ................ 424/442, 283.1, 424/130.1, 157.1, 158.1; 106/147.3, 148.1, 243; 426/89, 92, 140, 657; 530/388.24, 388.85, 389.2

[56] References Cited

U.S. PATENT DOCUMENTS

| | | | |
|---|---|---|---|
| 3,119,691 | 1/1964 | Ludington et al. | 99/2 |
| 4,357,272 | 11/1982 | Polson | 260/112 |
| 4,550,019 | 10/1985 | Polson | 424/85 |
| 4,748,018 | 5/1988 | Stolle et al. | 424/87 |
| 5,080,895 | 1/1992 | Tokoro | 424/85.8 |
| 5,428,072 | 6/1995 | Cook et al. | 514/460 |
| 5,725,873 | 3/1998 | Cook et al. | 424/442 |

FOREIGN PATENT DOCUMENTS

| | | |
|---|---|---|
| 0231817A2 | 8/1987 | European Pat. Off. . |
| 0241441A1 | 10/1987 | European Pat. Off. . |
| 0426463A2 | 5/1991 | European Pat. Off. . |
| WO9101803 | 2/1991 | WIPO . |
| 0556883A1 | 8/1993 | WIPO . |
| WO9421284 | 9/1994 | WIPO . |
| WO9604933 | 2/1996 | WIPO . |
| 0707798A1 | 4/1996 | WIPO . |
| WO9622028 | 7/1996 | WIPO . |

OTHER PUBLICATIONS

Albright, RB et al. Drug. Dev. Ind. Pharm. 20(12):2035–2039, Jul. 1994.

*Primary Examiner*—David Saunders
*Assistant Examiner*—F. Pierre VanderVegt
*Attorney, Agent, or Firm*—Quarles & Brady LLP

[57] ABSTRACT

A method of improving the efficiency of an animal to convert feed into desirable body tissue involves feeding the animal feed particles having an inner core of nutrients and an outer layer containing a conjugated fatty acid or an antibody that can protect the animal from contacting diseases that can adversely affect the animal's ability to grow or efficiently convert its feed into body tissue.

7 Claims, No Drawings

METHOD OF IMPROVING THE GROWTH OR THE EFFICIENCY OF FEED CONVERSION OF AN ANIMAL AND COMPOSITIONS FOR USE THEREIN

CROSS-REFERENCE TO RELATED APPLICATIONS

This application is a continuation-in-part application of application No. 08/684,785, filed Jul. 22, 1996, now U.S. Pat. No. 5,725,873, issued Mar. 10, 1998.

STATEMENT REGARDING FEDERALLY SPONSORED RESEARCH OR DEVELOPMENT

Not applicable.

BACKGROUND OF THE INVENTION

The present invention relates generally to the feeding of animals. More particularly, it relates to a method of improving the animal's growth or the efficiency of the animal to convert its feed into desirable body tissue (e.g. muscle) and compositions for use in the method.

It is known that healthy, disease-free animals grow faster or are more able to convert their feed efficiently into body tissue than sick or immune-challenged animals. Obviously, faster growth or a more efficient conversion of feed into desirable body tissue in an animal is both economically and ecologically important, especially in animals raised for food. For this, and other reasons, it is desirable to prevent animals from contacting diseases.

One approach to keeping animals healthy is to give the animals antibiotics. However, that approach is not desirable for animals raised for food because there can be antibiotic residues in the food.

Another approach to keeping animals healthy is to immunize the animals. This can be done by vaccinating the animals against specific diseases to produce an active immunization or by administering to the animals antibodies to produce a passive immunization.

In U.S. Pat. Nos. 4,748,018 and 5,080,895, methods are disclosed for passively immunizing animals against intestinal diseases which could interfere with the animal's efficient conversion of feed. The patented methods basically comprise orally administering to said animals effective amounts of egg-derived materials containing avian antibodies which are obtained by immunizing egg-laying hens with specific antigens which will produce such antibodies, and obtaining the antibody containing material from eggs laid by the hen. In both patents, the antibody containing egg materials are reduced to powders and fed to the animals to be passively immunized.

BRIEF SUMMARY OF THE INVENTION

It is the primary object of the present invention to disclose a novel method to improve the animals growth or the efficiency of the animal to convert its feed into desirable body tissue.

Another object of the invention is to disclose an animal feed for animals for use in the inventive method.

The method of the present invention to improve the animals growth or the efficiency of the animal to convert its feed into desirable body tissue comprises orally administering to said animal feed particles having an inner core comprising primarily non-fat nutrients and, on an outer surface of the inner core, a safe and effective amount of an antibody that help protect the animal from disease or other antigens that can adversely affect the animal's growth or the efficiency of the animal to convert feed into desirable body tissue. The particles can alternatively be coated with another compound that improves the efficiency of the animal to convert feed into desirable body tissue.

The compositions of the present invention are animal feed particles having an inner core comprised of nutrients, and, on an outer surface of the inner core, a compound that improves the efficiency of the animal to convert feed into desirable body tissue.

The compositions of the present invention are conveniently made by first forming a nutrient mixture to produce an inner core, and then depositing the compound on the outer surface of the core. Surprisingly, an antibody on the outer surface retains immunological activity and is not destroyed by antibody destroying factors, such as environmental conditions and intestinal proteases, even if the antibody is simply applied to the exterior of the pellet core without encapsulation in a protective fat layer.

In a preferred embodiment of the invention, antibodies are provided in solution or suspension in an aqueous or lipid carrier, although the antibodies can be applied directly to the pellet core without a carrier as, for example, a powder. The antibodies can be, but need not be, encapsulated in the lipid. The antibodies are obtained from the egg of a hen which has been injected with an antigen that results in the production by the hen of those antibodies.

Compositions of the present invention are superior to previously known animal feeds in which antibody-containing powders were mixed with nutrients, including fat, and then granulated or extruded, because the antibody-containing layer in the method of the present invention is applied to the core after the pelletization, extrusion, granulation or expansion process. As a result the antibodies in the outer layer of the compositions of the present invention are not degraded by elevated temperatures that can arise during pelletization, granulation, extrusion or expansion processes. The compositions of the present invention are also superior to prior art feeds. If the antibodies are mixed into an outer layer of fat, the fat helps protect the antibodies from stomach acid and intestinal enzymes. If the antibodies are not encapsulated in fat, they can be immediately released at high concentration into the gastrointestinal tract of the consuming animal and are not degraded upon ingestion.

BRIEF DESCRIPTION OF THE SEVERAL VIEWS OF THE DRAWINGS

Not applicable.

DETAILED DESCRIPTION OF THE INVENTION

In the preferred embodiment of the present invention, the animal feed particles comprise an extruded inner core which contains primarily the desired non-fat materials, such as proteins and carbohydrates, and an outer layer of a compound that improves the efficiency of the animal to convert feed into desirable body tissue. The compound is preferably an antibody which can be optionally encapsulated in a lipid layer. Another compound that can be provided on the outer surface is a fatty acid that improves feed conversion efficiency. A preferred fatty acid is an 18-carbon conjugated diene. A most preferred fatty acid is conjugated linoleic acid (CLA). The outer layer also can contain other ingredients, such as oil-soluble vitamins and the inner core can, of course, also contain fat, if desired.

In the preferred practice of the method of invention, the animal feed is orally fed to the animal in an amount which will passively immunize the animal or otherwise enhance the efficiency of feed conversion by the animal.

The antibodies for use in the present invention are those which can alter physiological processes that adversely affect growth and feed efficiency. They can be antibodies that are against diseases or specific endogenous regulators of food intake and gastrointestinal motility. The antibodies are preferably derived from the eggs of hens which have been previously immunized to produce those antibodies as described in U.S. Pat. Nos. 4,748,018 or 5,080,895. Especially preferred as the antibody-containing material are spray dried egg yolks and whole eggs. However, other non-egg derived antibody-containing materials may be used.

The free CLA isomers have been previously isolated from fried meats and described as anticarcinogens by Y. L. Ha et al., in Carcinogenesis 8(12):1881–1887 (1987). Since then, they have been found in some processed cheese products. Y. L. Ha, et al., J. Agric Food Chem. 37(1):75–81 (1987).

The free acid forms of the CLA may be prepared by isomerizng linoleic acid. The non-toxic salts of the free CLA may be made by reacting the free acids with a non-toxic base. Natural CLA may also be prepared from linoleic acid by the action of delta 12-cis, delta 11-transisomerase from a harmless microorganism such as the rumen bacterium *butyrivibrio fibrisolvens*. Harmless microorganisms in the intestinal tracts of rats and other monogastric animals may also convert linoleic acid to CLA (Chin, S. F. et al., FASEB J. v. 6, abstract #2665 (1992).

The CLA obtained by the practice of the described methods contains one or more of the 9,11-octadecadienoic acids and/or the 10,12-octadecadienoic acids and active isomers thereof. It may be free or bound chemically through ester linkages. The CLA is heat stable and can be used as is, or dried and powdered. The CLA is readily converted into a non-toxic salt, such as the sodium or potassium salt, by reacting chemically equivalent amounts of the free acid with an alkali hydroxide at a pH of about 8 to 9.

CLA can be a mixture of isomers of 9,11- and 10,12-octadecadienoic acid (c9, c11; c9, t11; t9, c11; t9, t11; c10, c12; t10, c12; c10, t12; and t10, t12) that would form from isomerization of c9, c12-octadecadienoic acid. As a result of the isomerization, only four isomers (c9, c11; c9, t11; t10, c12; and c10, c12) would be expected. However, of the four isomers, c9, t11- and t10, c12 isomers are predominantly produced during the autoxidation or alkali-isomerization of c9, c12 -linoleic acid due to the co-planar characteristics of carbon atoms around a conjugated double-bond and spatial conflict of the resonance radical. The remaining two c,c-isomers are minor contributors.

The relatively higher distribution of the t,t-isomers of 9,11- or 10,12-octadecadienoic acid apparently results from the further stabilization of c9, t11- or t10, c12-geometric isomers, which is thermodynamically preferred, during an extended processing time or long aging period. Additionally, the t,t isomer of 9,11- or 10,12-octadecadienoic acid that was predominantly formed during the isomerization of linoleic acid geometrical isomers (t9, t12-, c9, t12- and t9, c12-octadecadienoic acid) may influence the final ratio of the isomers or the final CLA content in the samples.

Linoleic acid geometrical isomers also influence the distribution of minor contributors (c,c-isomers of 9,11- and 10,12-, t9, c11- and c11, t12-octadecadienoic acids). The 11,13-isomer might be produced as a minor product from c9, c12-octadecadienoic acid or from its isomeric forms during processing.

The preferred inner core for the animal feed particles is an extrusion which contains a mixture of nutrients, such as grains, with or without added sugars, carbohydrates and/or proteins. The core will normally contain less than the desired total amount of the dietary fat for the animal because of the fat in the outer layer.

The fat for use in the outer layer can be any fat or lipid, which can be readily mixed with the antibody containing material to form a mixture, which contains the antibody therein and which can be readily sprayed or otherwise coated on the outer surface of the core. The antibody need not be directly on the surface of the inner core. Rather, one or more intermediate layers, comprising, for example, a binding agent, can be provided between the antibody and the core. Especially preferred are those fats which are solid at ambient temperatures and which will protect the antibodies from adverse environmental conditions and intestinal enzymes. Especially preferred as the fat is a mixture of tallow and CLA which increases feed efficiency.

Representative of other fats that can be used are the following:

Lard
Yellow Grease
Poultry Fat
Spent Restaurant Oil
Animal Oils
Vegetable Oils
Fish Oils
Oil Derivatives, i.e. lecithin
and
Mixtures thereof.

The practice of the present invention is further illustrated by the following examples:

EXAMPLE 1

Preparation Of Antibodies

An antigen, such as cholecystokinin peptide which produces cholecystokinin (CCK) antibodies, is injected intramuscularly into mature hens at a dose of about 50 μg to 1000 μg with a water-in-oil emulsion adjuvant. Samples of the whole eggs or yolks of eggs from the hens are assayed by known methods for CCK antibody content. When the CCK antibody titer reaches a maximum level, the whole eggs or yolks of eggs are collected and pooled, homogenized and spray dried to obtain a powder.

EXAMPLE 2

Preparation Of Animal Feed Particles With Outer Layer Of Fat Containing Antibodies A CCK antibody-containing powder made by the process of Example 1 is mixed with tallow to form a blend in which the powder is substantially encapsulated by the fat. The fat mixture is then spray coated upon inner cores made by the pelletization, the granulation, the extrusion or the expansion of a plasticized mixture of nutrients, including carbohydrate, protein and water. The resulting animal feed particles have an inner core of nutrients and an outer layer of fat containing CCK antibodies.

EXAMPLE 3

Animal Feeding Test

Ducks are fed the animal feed of Example 2 and their biological responses are determined. It is found that the ducks receiving the animal feed of Example 2 demonstrate an improved body weight gain and a more efficient rate of feed conversion than control ducks.

Table 1 shows the results obtained in 14 day old ducks fed a control feed and an otherwise identical feed (BRAVO) having an outer antibody-containing layer.

TABLE 1

ABOVE BODY WEIGHT SUMMARY

| TREATMENT | 14 day weight | 27 day weight | 14–27 day gain |
|---|---|---|---|
| Control | 0.66 kg | 2.03 kg | 1.37 kg |
| Bravo | 0.63 kg | 1.96 kg | 1.33 kg |

| TREATMENT | 39 day weight | 14–39 day gain | |
|---|---|---|---|
| Control | 3.15 kg | 2.49 kg | |
| Bravo | 3.23 kg | 2.60 kg | |

FEED CONVERSION DATA

| TREATMENT | 14–27 feed/bird | 0–27 feed/bw* | 14–17 feed/gain |
|---|---|---|---|
| Control | 2.50 kg | 0.558 kg | 1.826 kg |
| Bravo | 2.34 kg | 0.541 kg | 1.76 kg |

| TREATMENT | 14–39 feed/bird | 0–39 feed/bw* | 14–39 feed/gain |
|---|---|---|---|
| Control | 5.349 kg | 0.781 kg | 2.15 kg |
| Bravo | 4.930 kg | 0.695 kg | 1.90 kg |

*bw = body weight

EXAMPLE 4

A CCK antibody-containing powder made by the process of Example 1 were mixed with tallow to form a blend in which the powder was substantially encapsulated by the fat. The fat mixture was then spray coated upon the inner cores, as described in Example 2, at the indicated antibody levels.

Chickens were fed the animal feed and their biological responses were determined. Table 2 shows the results obtained in chickens fed the coated feed pellets (crumbles) for three weeks. Also shown are the results obtained when chickens were fed a standard feed mash containing the indicated amounts of the anti-CCK antibody.

In the course of the trial, both the rate of body gain and the feed efficiency were markedly higher in chickens fed the antibody-coated pellets than in those fed antibody-containing mash. Surprisingly, a superior increase is observed (relative to control feed) when the antibody is provided on pellets than as a component of mash.

TABLE 2

| Treatment | Week 1 Body Wt | Week 0–1 Body Wt Gain | Feed/Bird 0–1 Consumed | Feed/Body Wt | Feed/Body Wt Gain |
|---|---|---|---|---|---|
| Week 1 (Mash) | | | | | |
| Control | 132 | 93 | 124 | 0.938 | 1.344 |
| 0.075* Bravo | 136 | 97 | 132 | 0.969 | 1.368 |
| 0.25 Bravo | 138 | 98 | 131 | 0.947 | 1.338 |
| 0.75 Bravo | 127 | 87 | 125 | 0.984 | 1.442 |

TABLE 2-continued

| Treatment | Week 1 Body Wt | Week 0–1 Body Wt Gain | Feed/Bird 0–1 Consumed | Feed/Body Wt | Feed/Body Wt Gain |
|---|---|---|---|---|---|
| Week 2 (Crumbles) | | | | | |
| Control | 152 | 112 | 143 | 0.942 | 1.287 |
| 0.075 Bravo | 149 | 108 | 156 | 1.049 | 1.450 |
| 0.25 Bravo | 155 | 114 | 141 | 0.969 | 1.315 |
| 0.75 Bravo | 147 | 107 | 137 | 0.928 | 1.273 |
| Week 2 (Mash) | | | | | |
| Control | 311 | 272 | 384 | 1.237 | 1.421 |
| 0.075 Bravo | 329 | 290 | 400 | 1.218 | 1.386 |
| 0.25 Bravo | 323 | 283 | 396 | 1.226 | 1.401 |
| 0.75 Bravo | 291 | 251 | 353 | 1.244 | 1.451 |
| Week 2 (Crumbles) | | | | | |
| Control | 366 | 325 | 477 | 1.243 | 1.390 |
| 0.075 Bravo | 358 | 317 | 457 | 1.278 | 1.444 |
| 0.25 Bravo | 358 | 317 | 470 | 1.314 | 1.485 |
| 0.75 Bravo | 352 | 313 | 413 | 1.174 | 1.324 |
| Week 3 (Mash) | | | | | |
| Control | 624 | 584 | 823 | 1.316 | 1.406 |
| 0.075 Bravo | 635 | 595 | 845 | 1.334 | 1.423 |
| 0.25 Bravo | 608 | 568 | 835 | 1.375 | 1.473 |
| 0.75 Bravo | 569 | 529 | 787 | 1.382 | 1.488 |
| Week 3 (Crumbles) | | | | | |
| Control | 683 | 642 | 936 | 1.373 | 1.461 |
| 0.075 Bravo | 697 | 656 | 956 | 1.372 | 1.457 |
| 0.25 Bravo | 699 | 659 | 971 | 1.395 | 1.482 |
| 0.75 Bravo | 687 | 648 | 893 | 1.299 | 1.379 |

*grams of anti-CCK egg yolk per kilogram of feed.

EXAMPLE 5

Ducks were fed a pelleted diet on which either 0.5% corn oil (control) or 0.5% conjugated linoleic acid was sprayed on the outer surface of the pellets. The coated pellets were fed to 14 day old ducks for 13 days. Feed conversion (feed consumed per amount of gain) was determined from 14 to 27 days and 29 to 39 days of age.

TABLE 3

| Treatment | 14–27 day conversion | 29–39 day conversion |
|---|---|---|
| Control | 1.82 | 2.38 |
| CLA | 1.79 | 2.14 |

Feeding CLA from 14 to 27 days of age reduced feed conversion (pounds of feed per pound of gain). The effects of feeding pellets coated with CLA continued to have an effect even for the period between 29 to 39 days of age.

It will be apparent to those skilled in the art that the present invention can be used to prepare the animal feed for a wide variety of food animals or pets, including without limitation, ducks, chickens and turkeys.

It also will be readily apparent to those skilled in the art that a large number of changes and modifications can be made without departing from the spirit and scope of the present invention. Therefore, it is intended that the invention only be limited by the claims which follow.

We claim:

1. A method to improve the growth of an animal or the efficiency of an animal to convert feed into desired body tissue, said method comprising feeding an animal an effective amount of animal feed particles comprising an inner core of nutrients and having an outer surface, and a layer consisting essentially of unencapsulated antibodies on the outer surface of the inner core, said antibodies being antibodies that can passively immunize the animal against the adverse effects of an endogenous gut peptide which could reduce the animal's ability to grow or to efficiently convert its feed into desirable body tissue, wherein the method achieves superior growth or feed conversion than a second method wherein a comparable amount of the antibody is fed to the animal in an unpelleted form.

2. A method of claim 1 in which the antibodies are derived from a chicken egg.

3. A method of claim 1 in which the antibody is anti-cholecystokinin antibody.

4. A method to improve the growth of an animal or the efficiency of an animal to convert feed into desired body tissue, said method comprising feeding an animal an effective amount of animal feed particles comprising an inner core of nutrients and having an outer surface, and a layer consisting essentially of unencapsulated antibodies and conjugated linoleic acid on the outer surface of the inner core, said antibodies being antibodies that can passively immunize the animal against the adverse effects of an endogenous gut peptide which could reduce the animal's ability to grow or to efficiently convert its feed into desirable body tissue, wherein the method achieves superior growth or feed conversion than a second method wherein the antibody is fed to the animal in an unpelleted form.

5. A particulate animal feed comprising an inner core of nutrients, the core having an outer surface, and a layer consisting essentially of at least one unencapsulated antibody to an endogenous gut peptide on the outer surface of the inner core.

6. A particulate animal feed as claimed in claim 5 wherein the antibodies are anti-cholecystokinin antibodies.

7. A particulate animal feed comprising an inner core of nutrients, the core having an outer surface, and a layer consisting essentially of conjugated linoleic acid and at least one unencapsulated antibody to an endogenous gut peptide on the outer surface of the inner core.

* * * * *

UNITED STATES PATENT AND TRADEMARK OFFICE
CERTIFICATE OF CORRECTION

PATENT NO. : 5,919,451
DATED : July 6, 1999
INVENTOR(S) : Mark E. Cook and Daria L. Jerome It is certified that error appears in the above-identified patent and that said Letters Patent is hereby corrected as shown below:

<u>Column 1,</u>
Line 9, please delete the entire paragraph and insert therefor the following:
--     This invention was made with United States government support awarded by the following agencies:
    USDA 96-CRHR-0-6055
    The United States has certain rights in this invention. --

Signed and Sealed this

Ninth Day of December, 2003

JAMES E. ROGAN
*Director of the United States Patent and Trademark Office*